US00PP09292P

United States Patent [19]

Falstad, III

[11] Patent Number: Plant 9,292

[45] Date of Patent: Sep. 19, 1995

[54] *LEUCANTHEMUM*×SUPERBUM NAMED 'BARBARA BUSH'

[76] Inventor: Clarence H. Falstad, III, 152 Birchwood, Holland, Mich. 49423-6657

[21] Appl. No.: 184,999

[22] Filed: Mar. 28, 1994

[51] Int. Cl.[6] ..... A01H 5/00
[52] U.S. Cl. ..... Plt./74.1
[58] Field of Search ..... Plt. 68.1, 74.1, 82.1

[56] References Cited

U.S. PATENT DOCUMENTS

| | | | |
|---|---|---|---|
| P.P. 1,084 | 4/1952 | McMullen | Plt./68.1 |
| P.P. 1,125 | 9/1952 | Read | Plt./68.1 |
| P.P. 7,495 | 4/1991 | McDaniel | Plt./74.1 |

*Primary Examiner*—Howard J. Locker

[57] ABSTRACT

A variegated form of shasta daisy with a light yellow to cream-colored leaf margin.

2 Drawing Sheets

SUMMARY AND BACKGROUND OF THE INVENTION

This new variety of *Luecanthemum*×*superbum* represents a distinct clonal selection of the herbaceous perennial Shasta Daisy.

The new cultivar, *Leucanthemum*×*superbum* 'Barbara Bush', is named after the former First Lady with her permission, and is valued for its full season of appealing variegated foliage, and its attractive flowers and sturdy stems.

The plant orginated as a sport of *Leucanthemum*×*superbum* 'Thomas Killen'. In early 1988 a single variegated plant with a subtle yellow-green margin on green centered leaves was discovered in the greenhouse of a perennial nursey in Zeeland, Mich. This plant was one of several in a batch of tissue culture propagated plants produced at the same nursery. The subtle variegated shasta was introduced into tissue culture in August of the same year. Some plants of this type were produced, but because of the indistinct color pattern, I put little importance on production of these plants. In 1990 I discovered a few of the transplanted plants from one tissue cultured group of the above plants that had a brighter, more defined margin. I selected one of these specimens and began producing it in tissue culture in May 1991. Since that time I have asexually propagated the new improved form, now identified as *Leucanthemum*×*superbum* 'Barbara Bush', by division and through tissue culture.

The tissue culture methods used to propagate identical individuals are those techniques modified and improved by me at a nursery in Zeeland, Mich. Several Generations of plants have been reproduced, by tissue culture, which contain all the traits and characteristics of the original plant.

BRIEF DESCRIPTION OF THE DRAWINGS

The new cultivar is illustrated in the attached color photographs in which.

DETAILED DESCRIPTION OF THE NEW CULTIVAR

Figure 1:
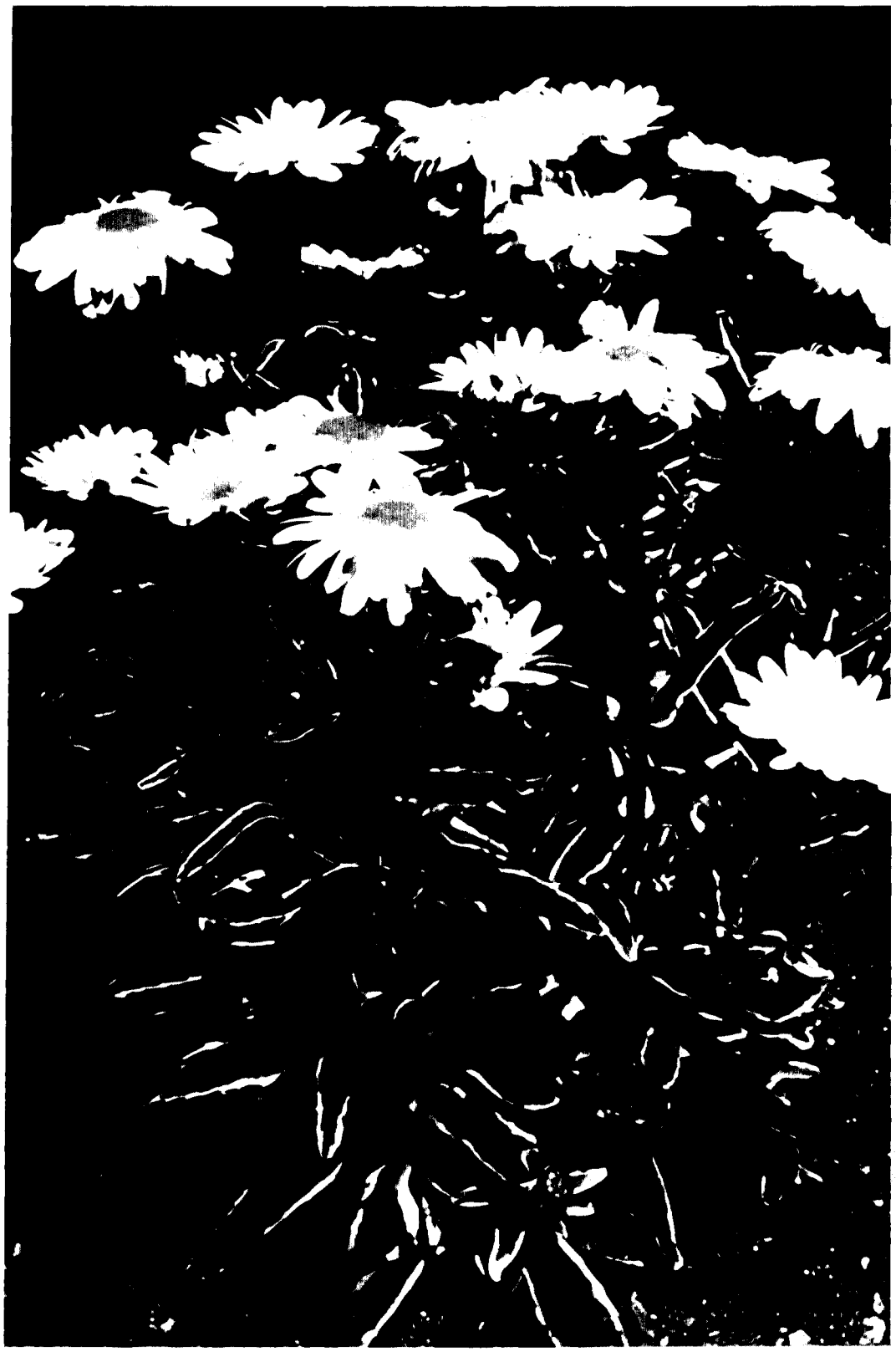
FIG. 1 shows the plant in flower, and growing in full sun in a test field; the second photograph.
Figure 2:
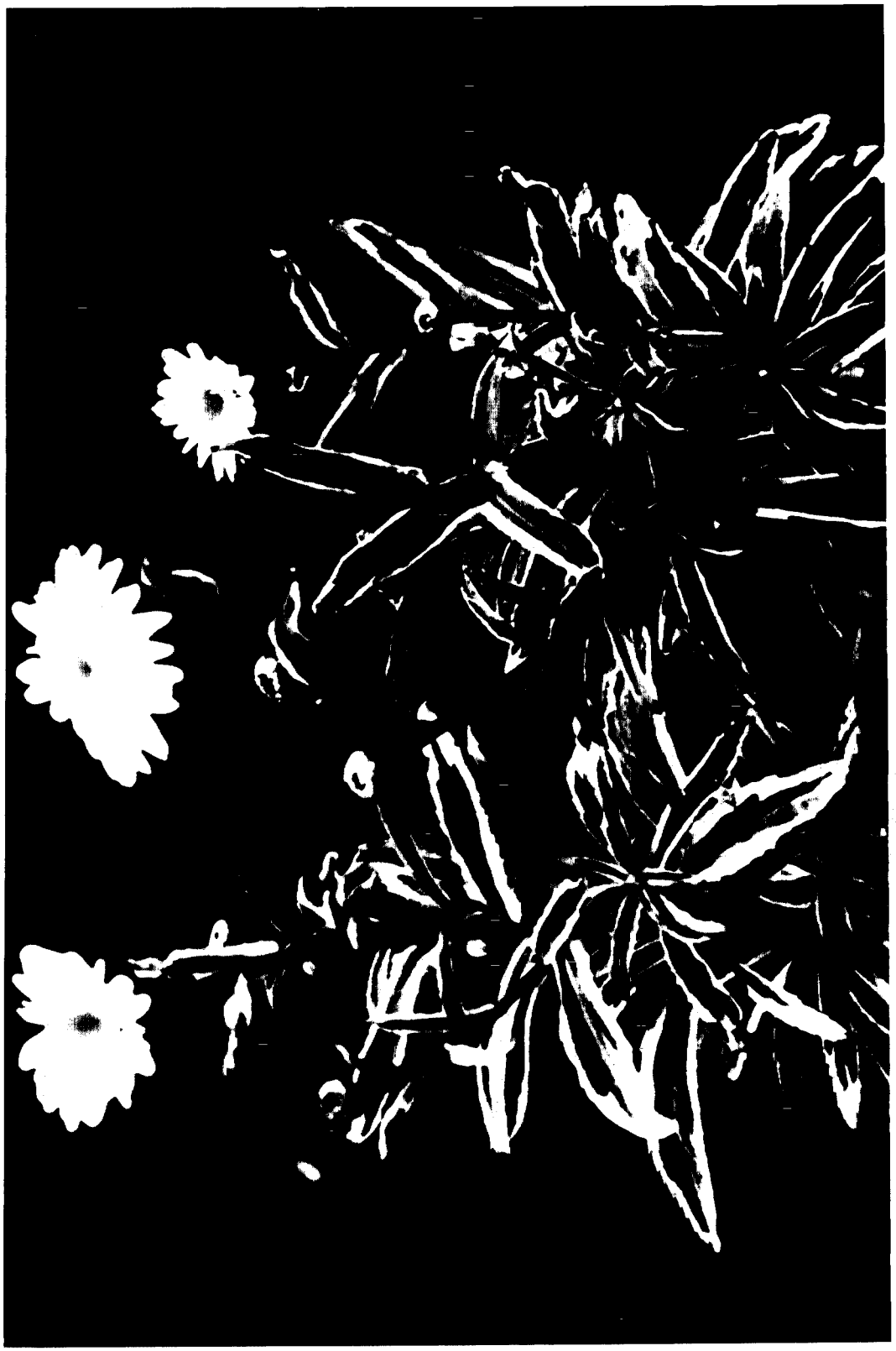
FIG. 2, represents a plant in flower, grown in light shade in a container, and photographed in sun for direct comparison.

The plant is described in detail using *The Royal Horicultural Colour Chart* with color description and corresponding reference number.

*Leucanthemum*×*superbum*'Barbara Bush' is a leaf chimera sport of the *Leucanthemum*×*superbum* "Thomas Killen'. 'Thomas Killen' is a large perennial shasta daisy characterized by the single white flowers composed of an outer row of ray florets, an inner row of smaller disc florets, and a row in between of ray florets with shorter split petals. It has strong flower stems reaching 75 cm (30inches). Flowering in western Michigan begins in late June and continues for about four to six weeks. Repeat flowering can occur in September and into October if the old flowers are removed shortly after blooming.

*Luecanthemum*×*superbum* 'Barbara Bush' is similar to its sport parent except that it is smaller and bears an attractive variegation. The plant size at flowering time is approximately 45 to 55 cm (18 to 22 inches) tall by 35 to 45 cm (14 to 18 inches) wide. Flowering time is identical to that of 'Thomas Killen'. Drought, and heat tolerance, as well as disease resistance is equal to that of 'Thomas Killen', and 'Barbara Bush' is hardy to at least −10° Fahrenheit.

*Luecanthemum*×*superbum* 'Barbara Bush' overall capitulum is approximately 5 to 8 cm (2½ inches to 3¼ inches) in diameter. The outer row of ray florets is between 32 and 38 mm (1¼ inches to 1½ inches) long, and up to 8 to 10 mm (5/16 to ⅜ inches) wide. The intermediate row of ray florets are 13 to 19 mm (½ to ¾ inches) long, and half as wide as the outer row of ray florets, 4 to 5 mm (⅛ to 3/16 inches). The color of the petals of both types of ray florets is clear white. The disc portion measures approximately 3 to 4.5 cm (1¼ to 1¾ inches) in diameter. The disc florets are about 6 to 10 mm (¼ to ⅜ inches) long and about 2 to 4 mm (1/16 to ⅛ inches) wide. The over all color of these disc florets in between Yellow Orange 14B and Yellow 12A on The Royal Horticultural Society Colour Chart. The disc flowers are generally complete whereas the ray flowers are generally missing the androecium.

The leaves of 'Barbara Bush' grown in shade are similar in color to those of early spring leaves. The basal leaves measure 11 to 13 cm (4.5 to 5 inches) long, and 2.5 to 3.5 cm (1 to 1.5 inches) wide. The margin of the shade grown plants is a yellow-green (R.H.S. 150B) and the center is a dark green (R.H.S. 137A). There is a white frosting that stretches over some of the green center in an irregular reticulate pattern producing a light grey green (between R.H.S. 147D and 148D). The distal leaves in the shade are the same colors withe the exception of showing less separation of the white frosting over the green center. The size of these leaves decreases as they get closer to the flower.

In full sun the basal leaves are 11 to 13 cm (4.5 to 5 inches) long and 2.5 to 3.2 cm (1 to 1.25 inches) wide. The secondary leaves are 3.8 to 10.8 cm (1.5 to 4.25 inches) long and 1 to 2.5 cm (0.3 to 1 inch) wide, and tend to diminish in size as the leaves get higher on the stem. The margin of the mature sun grown leaves is between Yellow 9D and 12D. The younger leaves on the stem are about a Yellow 9B. The leaf center is between a Green 138C and 137B on the basal leaves. The color of the secondary leaves is close to Green 141A.

I claim:

1. The new and distinct cultivar of perennial Shasta Daisy, or *Leucanthemum*×*superbum,* named 'Barbara Bush', substantially as herein described and shown, with a light gold to cream variegated margin, and suitable for landscape use, and as a potted plant.

* * * * *